United States Patent
Zengerle et al.

(10) Patent No.: US 9,725,758 B2
(45) Date of Patent: Aug. 8, 2017

(54) DEVICE AND METHOD FOR PRODUCING A REPLICATE OR DERIVATIVE FROM AN ARRAY OF MOLECULES, AND APPLICATIONS THEREOF

(75) Inventors: Roland Zengerle, Waldkirch (DE); Felix Von Stetten, Freiburg-Tiengen (DE); Guenter Roth, Freiburg (DE); Jochen Hoffmann, Freiburg (DE)

(73) Assignee: ALBERT-LUDWIGS-UNIVERSITAET FREIBURG, Freiburg (DE)

( * ) Notice: Subject to any disclaimer, the term of this patent is extended or adjusted under 35 U.S.C. 154(b) by 0 days.

(21) Appl. No.: 13/224,645

(22) Filed: Sep. 2, 2011

(65) Prior Publication Data
US 2012/0015844 A1 Jan. 19, 2012

Related U.S. Application Data

(63) Continuation of application No. PCT/EP2010/052849, filed on Mar. 5, 2010.

(30) Foreign Application Priority Data

Mar. 6, 2009 (DE) .................. 10 2009 012 169

(51) Int. Cl.
  *C12Q 1/68* (2006.01)
  *B01J 19/00* (2006.01)
  *C12Q 1/48* (2006.01)

(52) U.S. Cl.
  CPC ........ *C12Q 1/6837* (2013.01); *B01J 19/0046* (2013.01); *C12Q 2535/00* (2013.01); *C12Q 2535/122* (2013.01)

(58) Field of Classification Search
  CPC ............ C12Q 1/6837; C12Q 2535/122; C12Q 2535/00; B01J 19/0046
  (Continued)

(56) References Cited

U.S. PATENT DOCUMENTS 5,795,714 A * 8/1998 Cantor et al. ................ 435/6.15
6,017,738 A   1/2000 Morris et al.
(Continued)

FOREIGN PATENT DOCUMENTS

EP   1 203 945 B1   12/2006
JP   2001-183 A    1/2001
(Continued)

OTHER PUBLICATIONS

Margulies et al. (Nature, 2005, vol. 437, pp. 376-380, "Genome sequencing in micro-fabricated high-density picolitre reactors").*
(Continued)

*Primary Examiner* — Jeremy C Flinders
(74) *Attorney, Agent, or Firm* — Joyce von Natzmer; Agris & von Natzmer LLP

(57) ABSTRACT

A method of producing a replicate or derivative of an array of molecules, the array having a spatial arrangement of separate samples of molecules, includes creating, for each sample, at least one spatially limited effective area which is separate from the effective areas of the other samples, a surface, provided with a binding adapter or binding properties, of a carrier bordering on the effective areas. The molecules are amplified by means of amplifying agents in the effective areas for creating replicates or derivatives of the samples. The replicates or derivatives of the samples are bound to the carrier by means of the binding adapter or the binding properties, so that a spatial arrangement of the replicates or derivatives of the samples on the carrier corresponds to the spatial arrangement of the samples in the array. The carrier having the copies of the samples is removed from the array.

13 Claims, 8 Drawing Sheets

(58) Field of Classification Search
USPC .................................................. 506/7
See application file for complete search history.

(56) References Cited

U.S. PATENT DOCUMENTS

| | | | |
|---|---|---|---|
| 6,060,288 | A | 5/2000 | Adams et al. |
| 6,274,351 | B1 | 8/2001 | Peponnet |
| 6,300,070 | B1 | 10/2001 | Boles et al. |
| 6,514,768 | B1 * | 2/2003 | Guire et al. .............. 436/518 |
| 2003/0232382 | A1 * | 12/2003 | Brennan .............. C12Q 1/686 435/6.18 |
| 2005/0048580 | A1 * | 3/2005 | Labaer et al. .............. 435/7.1 |

FOREIGN PATENT DOCUMENTS

| | | |
|---|---|---|
| WO | 2006/088876 A2 | 8/2006 |
| WO | 2006/110855 A2 | 10/2006 |
| WO | 2008/022332 A2 | 2/2008 |
| WO | WO 2008022332 A2 * | 2/2008 |

OTHER PUBLICATIONS

Official Communication issued in International Patent Application No. PCT/EP2010/052849, mailed on Jun. 25, 2010.

English translation of Official Communication issued in corresponding International Application PCT/EP2010/052849, mailed on Oct. 7, 2011.

Yu et al., "Contact Printing Beyond Surface Roughness: Liquid Supramolecular Nanostamping," Advanced Materials, 2007, vol. 19, pp. 4338-4342.

Blanchard et al., "Cheap DNA Arrays—It's Not All Smoke and Mirrors," Nature Biotechnology, vol. 17, Oct. 1999, p. 953.

http://www.techno-preneur.net/technology/new-technologies/life-sciences/novel.htm.

Kim et al., "Transfer of Surface Polymerase Reaction Products to a Secondary Platform with Conservation of Spatial Registration," Journal of the American Chemical Society, 2006, pp. 12076-12077.

Kim et al., "Parallel Fabrication of RNA Microarrays by Mechanical Transfer from a DNA Master," Analytical Chemistry, vol. 79, No. 23, Dec. 1, 2007, pp. 8994-8999.

He et al., "Printing Protein Arrays from DNA Arrays," Nature Methods, vol. 5, No. 2, Feb. 2008, pp. 175-177.

Ramachandran et al., "On-Chip Protein Synthesis for Making Microarrays," Methods in Molecular Biology, vol. 328, 2006, pp. 1-14.

Shendure et al., "Next-Generation DNA Sequencing," Nature Biotechnology, vol. 26, No. 10, Oct. 2008, pp. 1135-1145.

Kane et al., "Patterning Proteins and Cells Using Soft Lithography," Biomaterials, 20, 1999, pp. 2363-2376.

Torres et al., "Gene Expression Profiling by Massively Parallel Sequencing," Genome Research 2008, 11 pages, (http://genome.cshlp.org/content/18/1/172.full?sid=d7c29131-aab2-45f5-8e10-681062e04f63#fn-group-1).

Wolfram, "Reach-Through Claims" und,, Reach-Through Licensing "-Wie Weit Kann Patentschutz auf biotechnologische Research Tools Reichen?," Mitteilungen der deutschen Patentanwalte, Feb. 2003, pp. 57-64.

http://www.cogenics.com/sequencing/service/pdf/titanium_lit.pdf, Genome Sequencer FLX System Workflow, copyright 2008.

Margulies et al., "Genome Sequencing in Microfabricated High-Density Picolitre Reactors," Nature, vol. 437, Sep. 15, 2005, pp. 376-380.

Mardis, "The Impact of Next-Generation Sequencing Technology on Genetics," Trends in Genetics, Elsevier Science Publishers B.V., vol. 24, No. 3, Feb. 11, 2008, pp. 133-141.

Morozova et al., "Applications of Next-Generation Sequencing Technologies in Functional Genomics," Genomics, 92, 2008, pp. 255-264.

Bing et al: "Bridge Amplification: A Solid Phase PCR System for the Amplification and Detection of Allelic Differences in Single Copy Genes", Genetic Identity Conference Proceedings, 1996.

Voelkerding et al, "Next-Generation Sequencing: From Basic Research to Diagnostics," Clinical Chemistry, 2009, 55:4, pp. 641-658.

Official Communication issued in corresponding Chinese Patent Application No. 201080019880.7, mailed on Apr. 26, 2013.

Peng et al., "Recent Developments in the Fabrication of DNA Microarrays," Physics, vol. 32, No. 9, Dec. 31, 2003, pp. 599-603.

* cited by examiner

DEVICE AND METHOD FOR PRODUCING A REPLICATE OR DERIVATIVE FROM AN ARRAY OF MOLECULES, AND APPLICATIONS THEREOF

CROSS-REFERENCE TO RELATED APPLICATIONS

This application is a continuation of copending International Application No. PCT/EP2010/052849, filed Mar. 5, 2010, which is incorporated herein by reference in its entirety, and additionally claims priority from German Application No. DE 102009012169.2-41, filed Mar. 6, 2009, which is incorporated herein by reference in its entirety.

BACKGROUND OF THE INVENTION

The present invention relates to methods and devices for producing a replicate or derivative from an array of molecules, such as biomolecules or chemically produced molecules, and, in particular, to such methods and devices that are suitable for producing a replicate or derivative of a microarray of said molecules and/or molecules derived therefrom, such as of a DNA microarray, RNA microarray or protein microarray, and to the application of the array for identifying DNA sequences associated with reactions involving primary sequences, copies thereof or derivatives thereof.

A microarray is understood to mean an arrangement of many different biomolecules on or in a surface in individual points. Said points are also referred to as spots and typically have a diameter ranging from 10 µm to about 1000 µm. One or several identical populations of biomolecules are present within a spot. Except for some intentional redundancies, the various spots, however, represent different biomolecules. The biomolecules may be deposited on the surface, may exist in a layer on the surface, may exist within a cavity, or may exist in an immobilized manner on or in a particle, it being possible for the particles to be arranged as an array.

Conventionally, there have been various techniques of producing microarrays. In accordance with one technique, the biomolecules are synthesized direct on the surface (in-situ synthesis), for example using light synthesis, chemical synthesis, spot synthesis, a printing process, and the like. Such a light-synthesis technique is employed, for example, by Affymetrix, spot synthesis is performed by Agilent. Combimatrix produces DNA microarrays by the means of virtual, electronically addressable reaction compartments. In accordance with a further technique, the (bio)molecules are at first synthesized and subsequently deposited on the surface as an arranged array, such a technique being employed, for example, by Agilent, Gesim and Biofluidix. Both techniques need a high level of technical expenditure. Said technical expenditure increases more than linearly as the number of different biomolecules increases and as the diameters of the deposition spots decrease. In addition, the amount of time involved as well as the costs increase significantly when such a microarray is to contain, e.g., twice as many substances, or if the size of the coated structures, i.e. spots, is to be reduced. A stamping technique for producing microarrays is described in [1].

By means of on-site synthesis on an array, it is possible to produce millions of different DNA sequences. However, in order to achieve a new layout or a different pattern size, it is needed to reorganize the entire manufacturing process. This will then need new instrument settings and, in the event of light-aided synthesis, even new photolithography masks or reprogramming of the digital minor system, see [2], where utilization of digital mirrors for creating a microarray is described. This is circumvented as far as possible in order to keep costs down.

For lack of time alone it is not possible to transfer more than a few tens of thousands of substances by means of synthesis in the laboratory and by means of subsequent transmission to a microarray, for example by means of a nanoplotter. It would take weeks or months to produce an appreciable number of dots on a microarray with a million different biomolecules. Whilst that time the surface chemistry will change and the whole microarray won't work any more.

Therefore, a method would be desirable by means of which it is possible to copy, in a simple and inexpensive manner, existing microarrays, that is, a regular arrangement of known biomolecules that are complicated and expensive to produce.

Some basic ideas on this issue have already been submitted, [3] and [4]. [3] and [4] disclose a method of replicating an oligonucleotide array wherein one or more biotin-functionalized oligonucleotides are hybridized into one or more oligonucleotides and amplified on a first substrate. The biotin-functionalized and amplified oligonucleotides are then anchored to a second substrate with streptavidin. The biotin-functionalized oligonucleotides may be separated from the oligonucleotides by mechanical force so as to create a replicated array. However, such copying processes are costly and need an additional biochemical anchoring system and in many cases could only produce a negative copy of the original DNA microarray.

[5] also describes copying of a DNA array by using a streptavidin/biotin system. [6] describes how DNA can be copied into RNA.

For about 30 years, DNA has been amplified in the laboratory. Inter alia, polymerase chain reaction (PCR) has made its arrival in almost all laboratories as a standard technique, and it is the foundation of most genetic studies. However, there are also other techniques enabling DNA to be multiplied, e.g. NASBA, recombinase polymerase amplification, rolling-circle amplification, and various other isothermal amplification techniques.

Not only do said techniques generally enable DNA to be multiplied, but they also enable targeted multiplication of individual DNA areas or subsets of the DNA. By means of specifically selecting the start points (primers), it is also possible to specifically multiply individual areas of the DNA. Most DNA amplification processes take place in solution, and this is referred to as a liquid-phase reaction. However, in the last few years, several methods have come up which utilize an additional solid phase for DNA amplification and in the process enrich same on said solid phase. E.g. the primer extension reaction on slide or solid phase [9,10]. In the following, two of the most common methods will be described, the foundations of bridge amplification of DNA as well as the water-in-oil emulsion PCR.

Bridge amplification of DNA: for bridge amplification, the (partly unknown) DNA is initially extended, at both ends, with known, so-called adapter sequences. Said extensions serve as binding sites for complementary sequences on the surface. It is only after binding to the surface has taken place that, later on, amplification will occur. The DNA strand that has been copied and, thus, newly created is now fixedly (covalently) bound to the surface, and has a further binding site at its non-bound end. Said further binding site may now also bind to a suitable counterpart on the surface and start a further amplification, which in turn will create a new DNA strand bound at one end and having the original binding sequence at the other, free end. In this manner, more and more new strands are generated, in an exponential manner, which are fixedly bound at one end, and whose other end enables temporary binding to the surface. During the amplification, the original strand is fixedly (covalently) bound at one end, and loosely (non-covalently) bound at the other end, and thus generates a molecular bridge. In this respect, [11] generally describes bridge amplification, and [12] describes utilization of bridge amplification for sequencing.

For a water-in-oil emulsion PCR, a type of bridge amplification is employed. This involves initially extending the DNA strands on both sides by means of adapter sequences, like for bridge amplification. Subsequently, the extended DNA is mixed together with an aqueous PCR mixture and solid-phase particles—also referred to as beads—and emulsified in oil, so that a water-and-particles-in-oil emulsion results. For this water-in-oil emulsion, the concentrations are selected such that ideally, precisely one DNA strand and precisely one particle will be trapped within each droplet of water. In accordance with bridge amplification, the surface of the particle contains sequences that enable a DNA copy to be covalently bound thereto. In this manner, the entire particle may be covered with copies of the original DNA by means of amplification. This technique is used mainly in sequencers. In this technique, only one single defined strand is amplified, at any one time, on the solid phase or liquid phase.

In protein amplification, or protein synthesis, there is a DNA strand that may basically be transcribed initially into RNA and then into a protein by means of a suitable biochemical system. If the RNA is sufficiently stable, or if there are a sufficient number of DNA templates, a large number of proteins can be produced. This technique corresponds to the natural process occurring within a cell which involves creating proteins from DNA via RNA, and it is the foundation and central paradigm of biochemistry. Since recently, simplified biochemical systems have been available which are capable of mastering this complex of tasks and thus enable producing, at least in principle, a protein from a DNA strand in the laboratory. In this respect, [7] describes a method of directly producing a protein microarray from a DNA microarray, and [8] describes a method of producing a protein microarray with cDNA anchors. Alternatively, protein amplification may also be performed using prokaryotic or eukaryotic cells which have protein-coding DNA introduced into them.

For decoding a DNA sequence, so-called sequencing methods are employed, an overview of relatively recent sequencing methods being provided in [13]. In addition, sequencing methods wherein DNA is bound to particles are described in [14].

The highly complex machines used for sequencing employ a multiplicity of reaction steps and techniques for initially trapping DNA that has been isolated, for multiplying it and for subsequently reading it out building block by building block. By means of the selected reaction chemistry and the sequencing method, it is possible, by means of expensive bioinformatics methods, to re-calculate the DNA sequence as a whole, and to thus obtain the genome of the species studied.

Previous sequencing techniques comprised splitting the DNA within a gel. This was an approach not based on solid phases and is called Sanger Sequencing. With the sequencers of the most recent generation, one works with a water-in-oil emulsion PCR and thus generates millions of particles, e.g. beads, which carry many identical copies of different DNA fragments, respectively. For reading out the sequence, the particles are arranged, e.g., in a so-called PicoTiterPlate™ having e.g. 1.3 to 3.4 million different microcavities, and are immobilized. This already represents a microarray as such. In this respect, please refer to [15], where utilization of bridge amplification for sequencing is described.

Even if a regular arrangement of biomolecules has already been produced in this manner, it nevertheless cannot be used like a conventional microarray with known sequences, since the individual sequences of the biomolecules bound to the particles are not yet known per se. However, after sequencing, the sequence of the DNA fragment bound to a specific particle will be known per se.

Efforts have already been made to retrieve the individual particles and reuse them as an array, for example on the part of Scineon together with the Max-Planck-Institut für Molekulare Genetik [*Max-Planck-Society for Molecular Genetics*] in Berlin. However, this method is costly and enables producing only one specimen of such an array.

Soft lithography, or microcontact printing, is a stamping technique that enables depositing molecules on a surface and to subsequently transfer same to another surface. It also enables integrating small cavities or microfluidics and to thus provide complex circuits for liquids. Said circuits enable treating surfaces in a specific manner and thus coating or modifying extremely small structures. The material used for this purpose is a silicone (PDMS). By means of suitable surface modification of the PDMS, various biomolecules can be added to the surface, and thus be transferred later on. Both DNA and RNA as well as biomolecules may be transferred.

These transfer properties may be exploited, inter alia, for a copying step, [16] being the first to describe how biomolecules may be transferred using soft lithography.

DNA arrays, or DNA microarrays, are mainly used for so-called expression analysis, sequencing and amount of genes or SNP analysis.

In expression analysis, one wishes to study the level of activity of specific genes. mRNA is considered to be a marker for this. For this purpose, cells or living beings are stimulated, for example by administering a drug, by changing environmental factors, by putting them under stress, and the like. From the biological material, one initially collects the mRNA, transcribes it into a so-called complementary DNA (cDNA), and provides it with a dye. A reference sample is provided with a different dye. Mostly, green and red dyes are used. Equal proportions of the samples are mixed together and then applied to the microarray. If a specific DNA sequence is contained, in equal concentrations, in both original samples, complementary molecules from both samples will bind, in equal concentrations, to the respective spot of the microarray. Reading out this spot therefore results in a secondary color. In the case of green and red, yellow will result. If there are unequal proportions of the same gene sequence, the corresponding spot on the microarray will comprise a secondary color whose coloration will represent the predominant gene product. Genes that are switched on or off completely will have only one hue or the other. The color pattern allows to infer the amount of mRNA and provides a clue as to how strongly specific genes have been activated or deactivated by the influences studied. [17] discloses application of expression profiling for genome-wide studies by means of highly parallel sequencings.

In SNP analyses, one investigates whether gene sequences comprise individual mutations, i.e. sequences that are identical except for one base pair (replacement of individual base pairs=single-nucleotide polymorphism). The precise location of the replaced base pair specifies whether the replacement has no or only minor effects on the organism, or whether this is a lethal gene defect. In the case of several serious hereditary diseases such as Huntington's Chorea, Parkinson's disease or Alzheimer's disease, such severe SNPs are known. With many other SNPs, one may infer increased risks or susceptibilities to specific diseases such as, e.g., diabetes or rickets. For SNP analysis, the DNA is directly collected from the biological material and marked with a dye. For each SNP, there are four spots on the microarray, which differ, in the same position in each case, by one base pair. From the basis of the binding position one can specify which base is in the relevant position in the unknown sample, see [17].

With protein arrays, production alone is considerably more difficult, since unlike DNA, proteins have an enormously broad spectrum of solubilities, reactivities and specificities. Therefore, it is not trivial to bind various proteins on a surface using the same chemical anchor. Typically, protein arrays contain several hundred to one thousand different proteins. Protein arrays are predominantly employed for binding studies. This comprises placing a marked molecule onto the protein array. Such spots on the microarray which comprise coloring are therefore potential binding partners for the molecule studied. This technique is employed, inter alia, for epitope mapping in order to specifically find binding sites.

The architecture of a microarray as such is described in [18].

The applications of microarrays are therefore far-reaching and manifold. However, due to the lack of the needed financial resources, or due to their cost-benefit ratio, they are restricted considerably in use.

DNA sequences contain biochemical information and may be multiplied by means of a biochemical replication system. Various approaches to copying DNA sequences have already been pursued, starting from copying the individual base pairs onto a surface, up to the approach described in [4], [5] and [6], which set forth how DNA can be copied, in principle, from one surface to another.

Also, an article [7] has recently been published about how a protein copy can be made from a DNA array.

The above illustrations show that the standard technology enables two fundamental techniques of producing microarrays, namely directly producing substances on site, on the one hand, and transferring the substances, after a synthesis, by means of a microscopic dispensing or printing process, on the other hand. Each of these techniques is technically complex and involves high expenditure in terms of time and cost, the general rule being that as the number of substances doubles, the time and cost needed will also at least double. In addition, to have precise knowledge of the biochemical information—in the case of DNA arrays, of the sequence—prior to synthesis is essential. To obtain said information in the case of DNA, so-called sequencers are used, as was explained above. No direct production chain between the sequencing and the fabrication of microarrays has so far been known or established. This means that an unknown organism is to be initially sequenced, whereupon the sequence is calculated from the data of the sequencer, and an array is subsequently produced. By means of this array immediately an expression pattern can then be studied. In addition, it is known to produce protein arrays from known sequences. This production chain is very protracted and costly.

If it was possible to generate protein arrays directly as a derivative of a DNA array by means of a simple method, the coupling between the phenotype and genotype would be retained, and it would be possible to perform reactions on the derivative in a spatially resolved manner (antigen-antibodies, enzymatic reactions) and to associate them with the underlying DNA sequence.

SUMMARY

According to an embodiment, a method of producing a replicate or derivative of an array of molecules, the array having a spatial arrangement of separate samples of molecules, may have the steps of creating, for each sample, at least one spatially limited effective area which is separate from the effective areas of the other samples, a surface, provided with a binding adapter or binding properties, of a carrier bordering on the effective areas; amplifying the molecules by means of amplifying agents in the effective areas for creating replicates or derivatives of the samples; binding the replicates or derivatives of the samples to the carrier by means of the binding adapter or the binding properties, so that a spatial arrangement of the copies or derivatives of the samples on the carrier corresponds to the spatial arrangement of the samples in the array; and removing the carrier having the replicates or derivatives of the samples from the array.

According to another embodiment, a utilization of a replicate or derivative that was produced while using a method of producing a replicate or derivative of an array of molecules, the array having a spatial arrangement of separate samples of molecules, may have the steps of creating, for each sample, at least one spatially limited effective area which is separate from the effective areas of the other samples, a surface, provided with a binding adapter or binding properties, of a carrier bordering on the effective areas; amplifying the molecules by means of amplifying agents in the effective areas for creating replicates or derivatives of the samples; binding the replicates or derivatives of the samples to the carrier by means of the binding adapter or the binding properties, so that a spatial arrangement of the copies or derivatives of the samples on the carrier corresponds to the spatial arrangement of the samples in the array; and removing the carrier having the replicates or derivatives of the samples from the array, either—for associating a reaction between a binder, in particular a protein, antibody or antigen, and an original molecule, its replicate or its derivative, with the DNA sequence of the original molecule, in particular for genotype-phenotype coupling, or—for associating a reaction wherein the original molecule, its copy or its derivative catalyzes the conversion of a substrate, with the DNA sequence of the original molecule, in particular for genotype-phenotype coupling, or—for identifying a DNA sequence, a RNA sequence, a protein or a catalytic, signaling (e.g. enhancing, allosteric, inhibiting . . . ) or enzymatic (e.g. lytic, phosphatase activity, kinase activity . . . ) function of a DNA, RNA or protein, or—for identifying a DNA sequence, a RNA sequence or a peptidic sequence and for producing, identification or preparation of a product, in particular antibody, antigen, vaccine or antibiotic, on the basis of the DNA, RNA or peptidic sequence, or—for detecting reactions between a sample, a replicate or derivative thereof with an interacting molecule or particle, said detection being performed by an optical, electrochemical or magnetic sensor, and the interacting molecule or particle carrying a corresponding marker, or said detection being performed, without any marker, via the change in the evanescent field or a modified resonance frequency, or by employing optical tweezers, or by coupling the reaction with a change in absorption, in particular precipitation or change of color, or with the emission of light, in particular chemiluminescence, or—for performing reactions on the replicate or derivative of the array, a chamber or fluidic structure having connecting terminals being applied over the surface of the replicate or derivative, or the replicate or derivative being introduced into a corresponding chamber, it being possible to incubate the chamber at a specific temperature, and to replace liquids included within the chamber, or—for simultaneously performing reactions and detections on the replicate or derivative.

According to another embodiment, a device for producing a replicate or derivative of an array of molecules, the array having a spatial arrangement of separate samples of molecules, may have a creator for creating, for each sample, at least one spatially limited effective area which is separate from the effective areas of the other samples, a surface, provided with a binding adapter or binding properties, of a carrier bordering on the effective areas; an amplifier for amplifying the molecules by means of amplifying agents in the effective areas for creating replicates or derivatives of the samples, and for binding the replicates or derivatives of the samples to the carrier by means of the binding adapter or the binding properties, so that a spatial arrangement of the copies or derivatives of the samples on the carrier corresponds to the spatial arrangement of the samples; and a remover for removing the carrier having the copies of the samples from the array.

Embodiments of the invention provide a method of producing a replicate or derivative of an array of molecules, the array comprising a spatial arrangement of separate samples of molecules, the method comprising:
creating, for each sample, at least one spatially limited effective area which is separate from the effective areas of the other samples, a surface, provided with a binding adapter or binding properties, of a carrier bordering on the effective areas;
amplifying the biochemical molecules by means of amplifying agents in the effective areas for creating replicates or derivatives of the samples;
binding the replicates or derivatives of the samples to the carrier by means of the binding adapter or the binding properties, so that a spatial arrangement of the copies or derivatives of the samples on the carrier corresponds to the spatial arrangement of the samples in the array; and
removing the carrier comprising the copies of the samples from the array.

Embodiments of the invention provide a replicate or derivative of an array of molecules that was produced by using a corresponding method.

Embodiments of the invention provide a device for producing a replicate or derivative of an array of molecules, the array comprising a spatial arrangement of separate samples of molecules, the device comprising:
means for creating, for each sample, at least one spatially limited effective area which is separate from the effective areas of the other samples, a surface, provided with a binding adapter or binding properties, of a carrier bordering on the effective areas;
means for amplifying the biochemical molecules by means of amplifying agents in the effective areas for creating replicates or derivatives of the samples, and for binding the replicates or derivatives of the samples to the carrier by means of the binding adapter or the binding properties, so that a spatial arrangement of the replicates or derivatives of the samples on the carrier corresponds to the spatial arrangement of the samples in the array; and
means for removing the carrier comprising the copies of the samples from the array.

In accordance with the invention, a spatially limited effective area, which is separate from the effective areas of the other samples, is made available to each sample of an array of molecules, for example of a DNA microarray, so that the present invention enables producing a replicate or derivative of a corresponding array in a fast, simple and inexpensive manner while retaining the positional information that is given by the spatial arrangement.

In particular, embodiments of the invention relate to corresponding methods and devices wherein the molecules are biomolecules or synthetically produced chemical molecules. In accordance with the invention, a replicate can be understood to mean a 1:1 copy of the original molecules, whereas derivative can be understood to mean a change in the original molecules, for example descendants or subsets of the original molecules. In accordance with the invention, samples of molecules may be understood to mean different molecules arranged at the different sites of an array, or different mixtures of molecules arranged there.

Embodiments of the invention enable copying microarrays without having any knowledge of the biochemical information, that means also copying non-synthetical microarrays, in particular. This enables copying out, from sequencers already, a copy of the arrangement of DNA present there, and thus providing a DNA array without having any knowledge of the sequences.

Thus, embodiments of the present invention enable producing a corresponding microarray prior to, following or during a sequencing process, even without having any knowledge of the sequences of the individual samples. Thus, the time-consuming and costly process step of synthetically generating an array may be circumvented, and an array may be produced directly from the sequencing. Embodiments of the invention thus enable multiplying a given microarray or coating pattern in a fast manner and independently of whether any biochemical sequences or information of the microarray are known. Embodiments of the present invention also enable producing different variations from one and the same original, as may be needed for different tasks set, since different biomolecules, for example DNA, RNA or proteins, are used for different biochemical issues. So far, it has not been possible to produce a suitable DNA or even protein microarray prior to, during or following to a sequencing process.

Embodiments of the invention enable producing, by means of a biochemical copying process, a secondary microarray directly from a primary material, for example a primary array of particles, prior to, during or following a sequencing process, and biochemically mapping said secondary microarray to DNA, RNA or proteins once again in the form of a further array, if need be. In addition, during different copying steps, variations of the arrays may be produced in a chemical form, which contain, for example, specific markers or sequences, comparable to a color copy, were only the yellow part of a picture could be copied.

Embodiments of the present invention relate to the production of a copy of a microarray from an arrangement of DNA sequences from a sequencing process (e.g. particle array in a sequencer by ABI or Roche 454), which has so far been neither described nor performed. Even though individual sub-steps, such as biochemically copying from DNA to DNA or from DNA to protein, have been described in standard technology, it is not known, however, to combine individual sub-steps for producing a microarray from a sequencing process. In particular, a production line of sequencing, followed by production of DNA arrays by fabricating a replicate from a DNA array from the sequencer, followed by the production of an RNA array or protein array from the DNA array, has not been known so far.

As was already illustrated, it is not known from standard technology to produce a DNA array already from an ongoing sequencing process. Also, it has not been described so far to copy said DNA array directly and then to reform it, by means of selective modifications, into subsets of DNA or RNA microarrays up to protein microarrays. Embodiments of the invention enable, for the first time, producing a DNA array during a sequencing process and converting it immediately to any array surfaces desired so as to thereby enable any common microarray studies. In embodiments of the invention, laborious synthetic production of microarrays may be completely circumvented in this manner.

However, embodiments of the invention are not limited to copying a microarray from a sequencing process. Rather, embodiments of the invention enable directly copying a planar microarray, such as, e.g., a commercially available microarray, in a simple manner and at low cost. Embodiments of the invention enable selectively copying out aspects of arrays and transcribing them so as to create RNA, DNA subset, cDNA or protein arrays.

Suitable copying methods, such as suitable amplifying means (e.g. PCR, isothermal amplification, NASBA) and respectively matching binding adapters or binding properties of the surface (e.g. primers, streptavidin/biotin, antigen-antibodies, polyhistidine/nickel complexes, electrostatic/dynamic or magnetic properties) are obvious to a person skilled in the art and need no further explanation to be given herein. In this respect, please also refer to the documents mentioned in the introduction, whose teachings on this matter shall be incorporated herein by reference.

In accordance with embodiments of the present invention, at least one copy of the genetic information, for example of the DNA, is thus produced from genetic information that may be referred to as a primary array, which copy may be referred to as a secondary array. A further array copy, which may be referred to as a tertiary array, may again be produced from the copy. The tertiary and/or the secondary array may either be an identical copy, a complementary copy, a subset, or an RNA or protein array, depending on the choice of the biochemical replication system with regard to the primary and/or secondary array.

In embodiments of the invention, the primary array originates from a DNA sequencer. Basically, any commercial particle-based sequencers may be considered for this. In alternative embodiments, however, any planar DNA microarrays may be used as primary arrays that are to be copied. Embodiments of the invention relate to any "copying process" from any one surface to another, provided that each sample of the array has a spatially limited effective area made available to it that is separate from the other effective areas. This includes any substance libraries ordered in a spatially resolved manner which contain biochemical information, which includes, in addition to the planar microarrays, also non-planar surfaces or particle arrays, for example, as are produced in sequencers or in chemical substance libraries.

In embodiments of the invention, the amplifying agents used may be any known amplifying agents. Previous amplifications have aimed at multiplying specific DNA segments or sequences. With such known amplifications, the positional information about where a particular strand was produced typically is not retained, since said amplifications take place in solution. In embodiments of the invention, by contrast, the positional information from the source, i.e. the primary array, to the copy, i.e. to the secondary array, is entirely or partly retained in the production of the replicate in that each sample has a spatially limited amplifying agent area, that is separate from the amplifying agent areas of the other samples, made available to it. This positional information is frequently also referred to as registration. This is understood to mean, e.g., the position of a specific DNA segment as defined by its arrangement (row and column, or x and y positions) within a regular grid. Due to this at least partial retention of the positional information, the present invention enables production of high-quality replicates. The more positional information is retained, the better the replicate will be. A poor spatial resolution will create, when multiple copies are made, copies that are of increasingly poor quality and will consequently be useless at some point.

In accordance with the invention, any known amplification methods may generally be employed; in some embodiments, a PCR or a bridge amplification may be used. Bridge amplification may be used on a surface. In embodiments of the invention, the copying process therefore represents some kind of bridge amplification which, however, takes place from one surface to another, the positional information, or the registration of the copied species, being retained. In alternative embodiments, an additional binding system may also be used for binding the copies to the carrier, for example a streptadivin/biotin system as is described in [4], which, however, results in increased complexity.

In embodiments of the invention, the binding adapters may be arranged over the entire area of the carrier to which the array is to be copied.

In embodiments of the invention, the binding adapters are primers that are complementary to sequences of the molecules to be copied.

In embodiments of the invention, retention of the positional information is achieved by spatially separating or compartmentalizing the amplifying agent areas associated with the respective samples. In this manner, individual molecules may be prevented from escaping from the "microcompartment", so that the spatial resolution or registration is retained. As was already explained, in embodiments of the invention, any amplification techniques may be considered as the copying process, such as PCR or isothermal amplification. During the copying process, the duplicate is deposited onto a target surface and anchored. In addition to the fact that the genetic information is entirely or partly retained, the positional information is also retained. Embodiments of the invention provide a 1:1 replicate, which generally is understood to mean "simple" copying of the surface. In this process, a copy of the original is produced which has the highest level of similarity possible. In the case of microarrays, after the copying process one will have obtained a further DNA array from a DNA array.

Embodiments of the invention enable producing a partial replicate, i.e. a derivative, of an array. A partial replicate or a partial copy is understood to mean a specific selection of the information copied. For example, during the process of copying a DNA array, only a specific type of DNA can be multiplied by selecting primers that the carrier comprises as binding adapters. In this manner, a subset is achieved that contains the information desired, such as all of the DNA strands that contain a specific sequence or a specific promoter.

Likewise, a derivative is referred to as a "conversion" of the copy of a DNA to an RNA or cDNA, of an RNA to a DNA, cDNA or to a protein. In this context, the biochemical information is transformed from one type of molecule to another, and the positional information is still retained.

In embodiments of the invention, the limited effective areas in the form of spatially limited amplifying agent areas are created by solid structures, whereas in alternative embodiments of the invention, phase boundaries between liquids of different levels of viscosity contribute to creating the spatially limited effective areas.

In addition, embodiments of the invention relate to applications of corresponding replicates and derivatives for analytical purposes, with regard to their reactions or interactions with other molecules or particles, and with regard to reaction catalysis.

BRIEF DESCRIPTION OF THE DRAWINGS

Embodiments of the present invention will be explained below in more detail with reference to the accompanying figures, in which.

DETAILED DESCRIPTION OF THE INVENTION

Figure 1A:
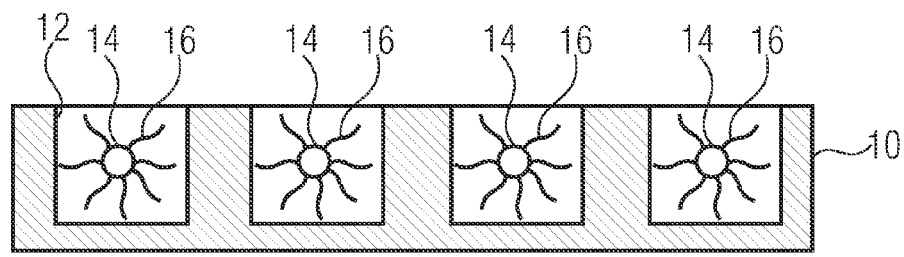
FIGS. 1a to 1d are schematic cross-sectional representations for illustrating an embodiment of the inventive method.
Figure 1B:
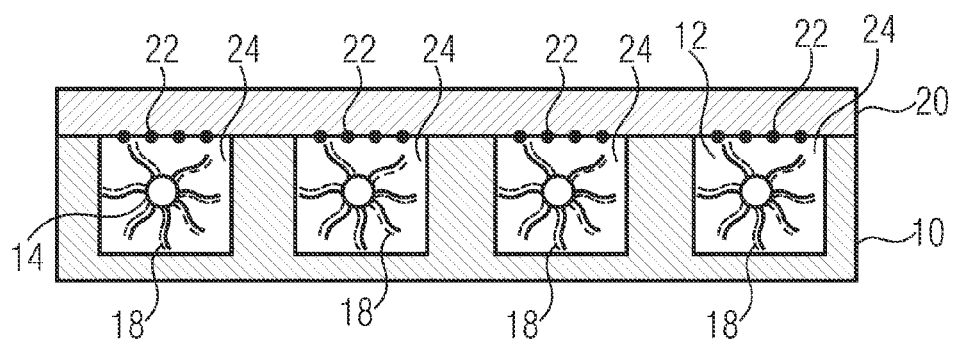
Figure 1C:
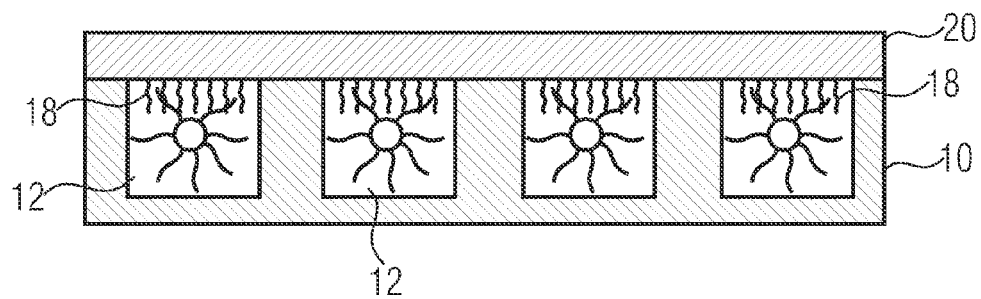
Figure 1D:
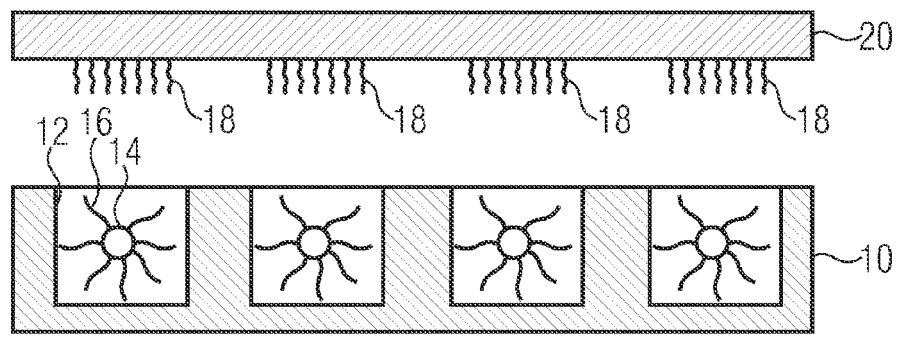
Figure 2:
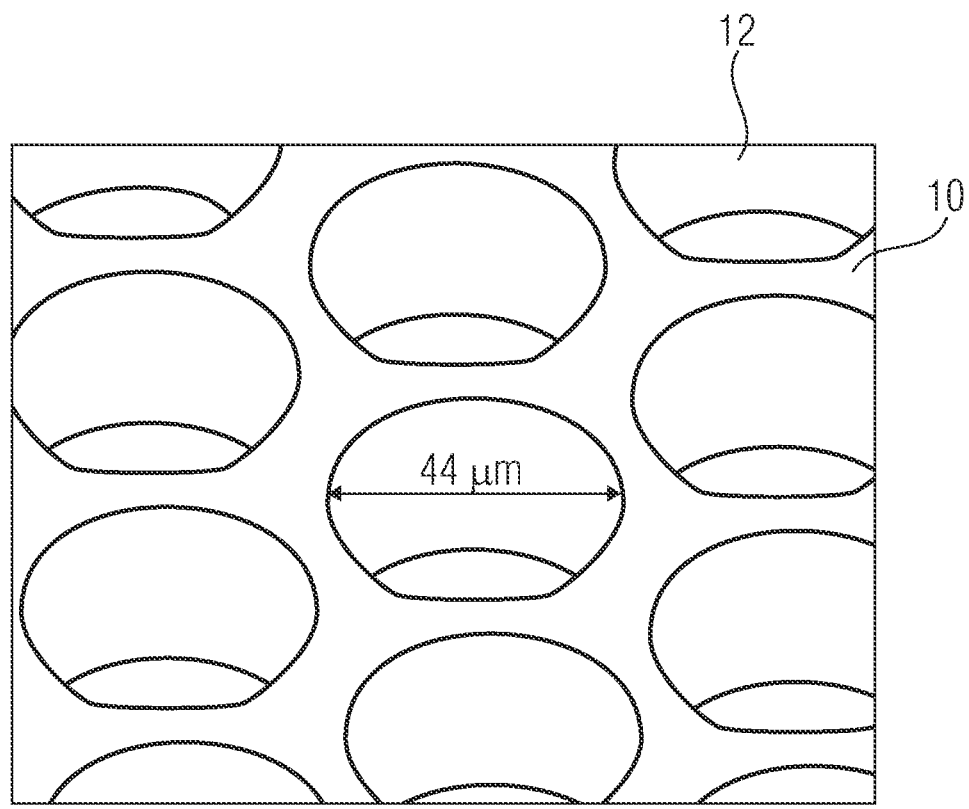
FIG. 2 schematically shows a top view of a section of a PicoTiterPlate™.

With reference to FIGS. 1a to 1d, an embodiment of an inventive method will be described below, wherein the primary array exists in the form of a sequencer chip 10. The sequencer chip 10 comprises a plurality of microcavities 12. A schematic top view of a section of the sequencer chip 10 comprising the microcavities 12 is shown in FIG. 2. The microcavities may have a diameter of 44 μm or 29 μm, for example, as is shown in FIG. 2. The sequencer chip may be, for example, a sequencer chip (GS FLX 2005 and/or GS FLX Titanium 2008) of the 454 sequencer by Roche.

Figure 3:
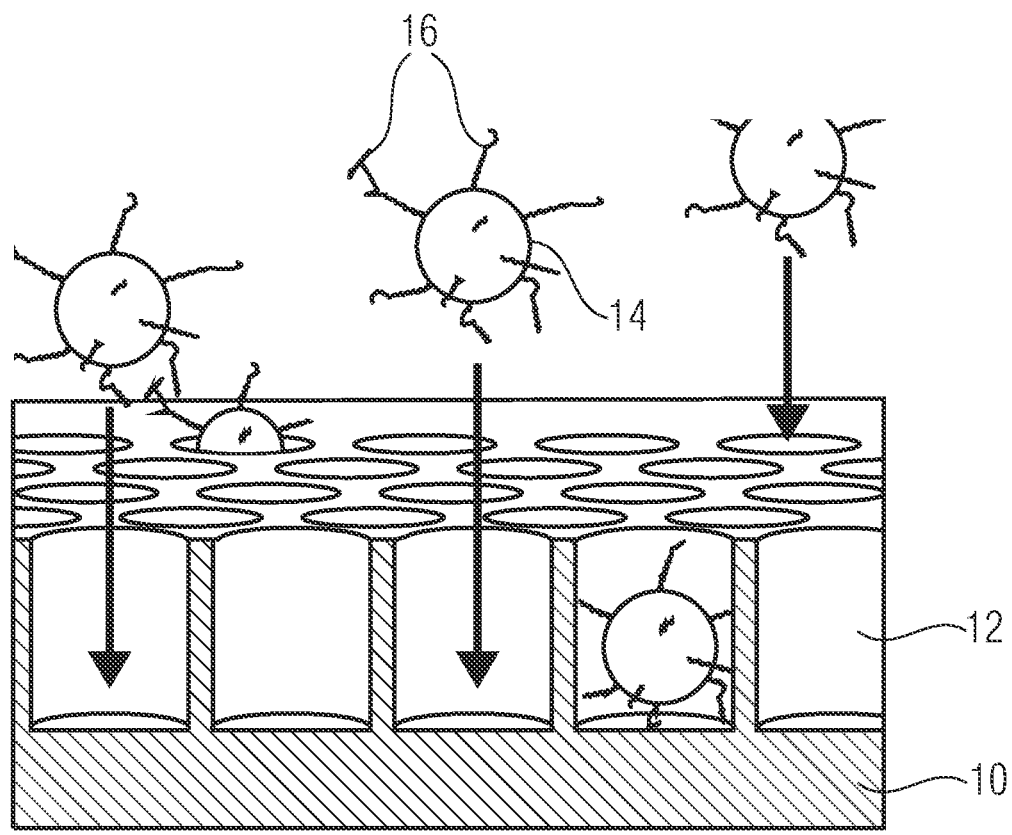
FIG. 3 schematically shows a cross-sectional representation of a sequencer chip comprising DNA particles.

Each of the cavities 12 has a particle 14 disposed therein, each of said particles 14 carrying millions of copies of an individual DNA strand 16. A schematic cross-sectional representation of the sequencer chip 10 comprising the cavities 12 which have the particles 14 comprising the DNA strands 16 introduced into them is shown in FIG. 3. Until now, the sequencer chips have been discarded after the sequencing process and have therefore been "waste products" of sequencing processes.

In the embodiment depicted in FIGS. 1 to 3, this chip is used as a primary array for producing a replicate. The DNA is to be copied out from the cavities 12. For this purpose, the cavities are initially filled with an amplifying agent, for example a PCR mix. Subsequently, as is shown in FIG. 1b, a carrier 20 is deposited which seals the cavities 12 and which carries binding adapters matching the amplifying agent, schematically shown as spots 22 in FIG. 1b. Once the cavities 12 have been closed off by the lid 20, a spatially limited amplifying agent area 24 has thus been produced for each sample, i.e. each particle 14 having DNA strands 16 bound to it, which amplifying agent area 24 is separated from the amplifying agent areas 24 of the other samples. The binding adapters 22 border on these amplifying agent areas 24. For example, the binding adapters 22 are primers matching the PCR mix. Said primers are binding sites for DNA polymerase. FIG. 1b shows the state after the polymerase step wherein biochemical copies are made of the particle's DNA. These copies are depicted as dashed lines 18 in FIG. 1b. For example, by means of the selection of the primers, a mixture of enzymes used as an amplifying agent may produce, in this step, a complementary DNA, i.e. a negative copy.

Subsequently, the copies 18 of the DNA that have been made are released from the particles 14, which may be performed, for example, by heating the sequencer chip and, thus, the cavities arranged therein. Thereafter, the released copies 18 add to the binding adapters 22, which may be promoted, for example, by cooling the sequencer chip. The result of the copies 18 adding to the binding adapter 22 and, thus, to the carrier 20 is depicted in FIG. 1c. In this step of copying the copies to the carrier 20, the positional information, or the registration, is retained, since a spatially limited amplifying agent area 24 is provided for each sample, and since the amplifying agent areas 24 are separate from one another.

Subsequently, the carrier 20 with the DNA copies 18 bound to it is removed from the sequencer chip 10 and represents a replicate of the DNA particle 14, 16 arranged within the cavities 12 of the sequencer chip 10. The particles 14 comprising the DNA strands 16 remain within the cavities 12, so that said cavity may again serve as a primary array for a new copying process with a new carrier. In this manner, basically any number of copies may be produced. The carrier 20 having the DNA copies 18 bound to it may be employed, for example, as a biochip in a transcriptome analysis, in detection of binding of proteins onto DNA, RNA onto DNA, or even RNA onto RNA.

So as to once again prepare, after the copying process, the primary array (the sequencer chip 10) for a further copying cycle, the amplifying agent within the cavities, e.g. the PCR mixture, may be replaced or removed. To avoid contaminations a washing step, which may also contain enzymes (like the uracil-N-glycosylase, which digest special DNA products), removes the PCR products and allows as such more copies without contaminating the original master.

Figure 4A:
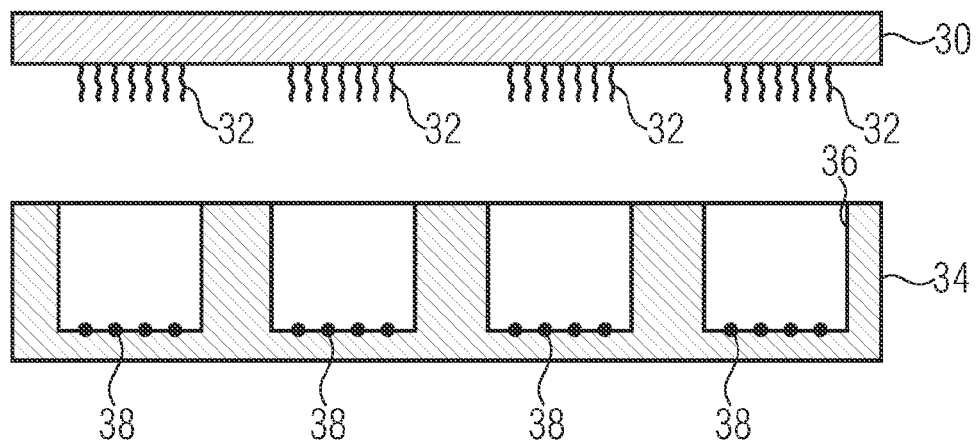
FIGS. 4a to 4c schematically show cross-sectional representations for illustrating a further embodiment of the inventive method.
Figure 4B:
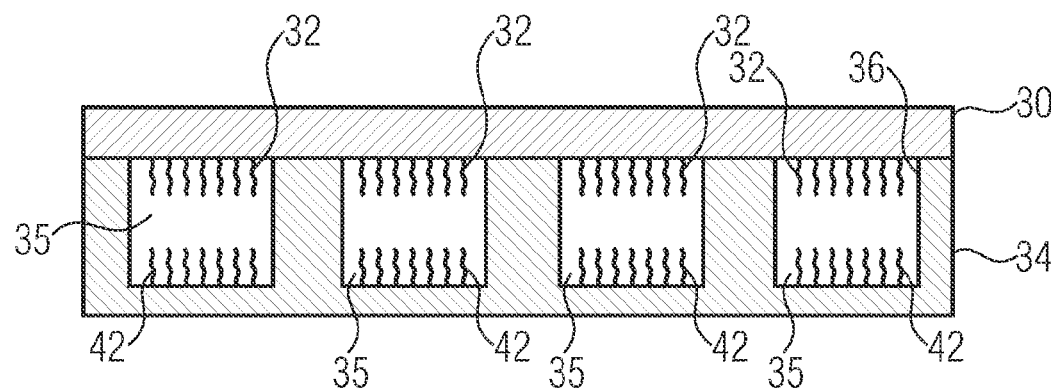
Figure 4C:
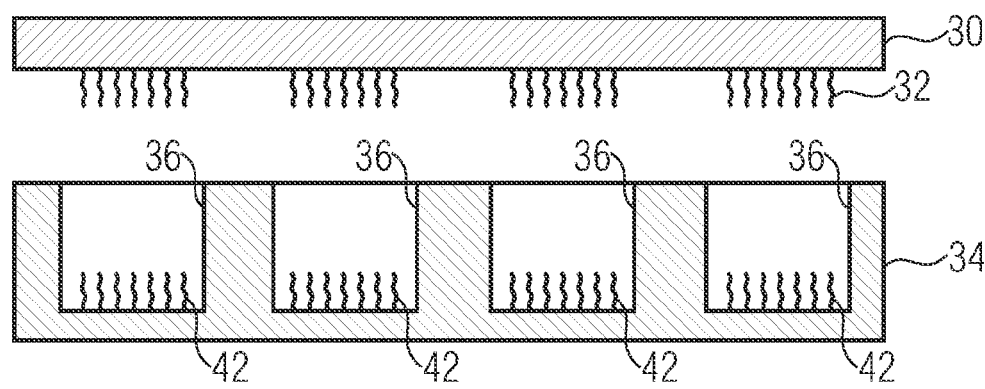

FIGS. 4a to 4c depict a further embodiment of an inventive method, wherein a conventional planar microarray serves as a primary array. The planar microarray is arranged on an array substrate 30 and contains the desired DNA samples. The DNA samples have a two-dimensional spatial arrangement. For the process of copying the DNA samples, a microstructure 34 comprising cavities 36 is provided. At least one cavity 36 is provided for each DNA sample 32. To obtain a relatively high resolution, a plurality of, in each case, relatively small cavities 36 may be provided, in alternative embodiments, for each DNA sample 32. The cavities 36 have binding adapters 38 arranged therein.

The cavities, or microcavities, 36 are filled with an amplifying agent, for example a polymerase mixture. The microstructure 34 is then deposited onto the microarray 30, so that the cavities 36 are closed off by the array substrate 30 (a small distance would also work but would enhance contaminations between cavities), and such that the DNA samples are arranged within the cavities 36 associated with them, respectively. In this manner, a spatially limited amplifying agent area 35, which is separate from the amplifying agent areas 35 of the other samples, is produced, again, for each DNA sample. The binding adapters 38 may again be formed, again, by a primer matching a polymerase mixture.

After producing the amplifying agent areas 35 thus closed off, an amplification like the polymerase step takes place once again, wherein the DNA samples 32 are multiplied and copied into the cavities 36. The copied DNA is anchored at the binding adapters 38, as is schematically shown by the DNA 42 in FIG. 4b. To this end, again, the temperature of the cavities having the DNA samples arranged therein may be controlled accordingly. Finally, the DNA substrate 30 having the DNA samples 32 located thereat is removed from the microstructure 34, so that the microstructure 34 with the copied DNA 42 represents a replicate of the original microarray. The microstructure 34, which is thus loaded with the copied DNA 42, may now be used as a template for further copying steps which may be performed, for example, analogously with the method as was described above with reference to FIGS. 1a to 1d. In this context, the microstructure 34 may be configured such that after the copying process it will have the same properties as a sequencer chip, for example the sequencer chip from the 454 sequencer by Roche.

An embodiment may comprise a combination of the methods in accordance with the above-described embodiments. Initially, a sequencer chip may be used for producing, by a copying process in accordance with the above FIGS. 1a to 1d, a planar carrier comprising a microarray of the entire DNA. Subsequently, this carrier is copied once again in accordance with the embodiment described with reference to FIGS. 4a to 4c. The microcavities thus occupied by DNA (microcavities 36 in FIGS. 4a to 4c) may now be used for producing further copies of the DNA, for example in accordance with the method of FIGS. 1a to 1d. Alternatively, the microcavities occupied by DNA may be used for producing modified copies in the form of complementary DNA, subgroups of DNA, shortened, extended or modified DNA, or even RNA up to proteins. In this manner, any areas comprising DNA, RNA or proteins or peptides may be produced.

Figure 5A:
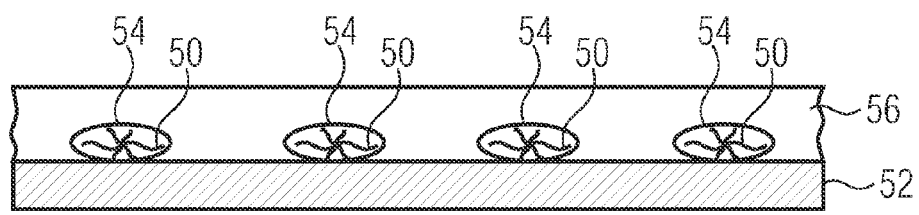
FIGS. 5a to 5d schematically show cross-sectional representations for illustrating a further embodiment of the inventive method.
Figure 5B:
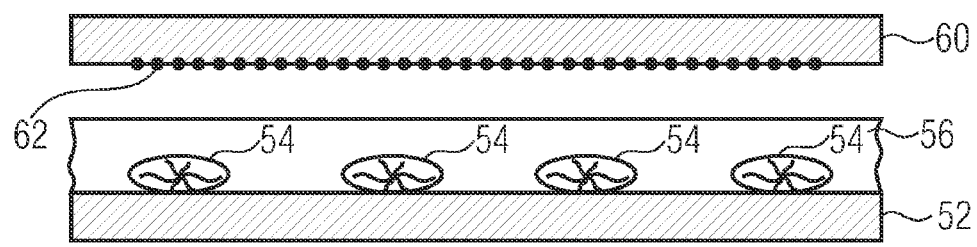
Figure 5C:
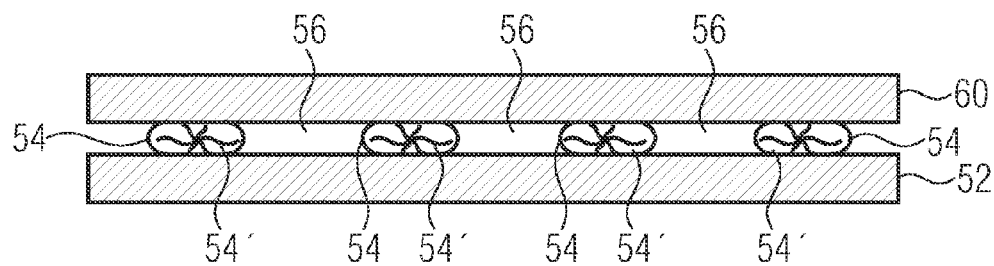
Figure 5D:
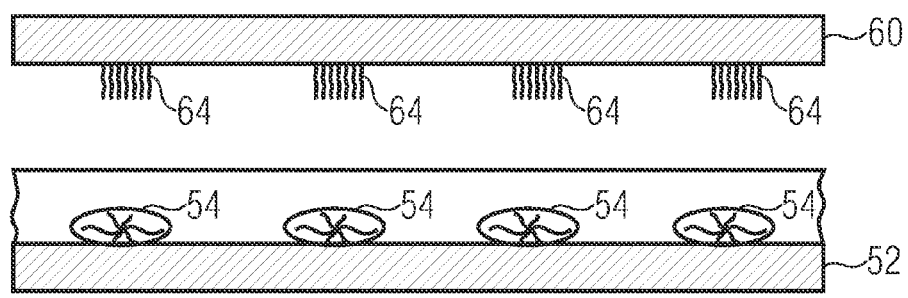

A further embodiment of an inventive method will now be described with reference to FIGS. 5a to 5d. In this embodiment, DNA is multiplied into individual particles 50 by means of a water-in-oil emulsion PCR. One type of DNA is anchored per particle (like in the preparation of the beads for the 454 sequencing or in the ABI SOLID sequencer). Said particles are placed on a surface of a carrier 52. More specifically, the particles 50 are located in respective droplets of liquid 54, for example droplets of water. The droplets of water are separated from one another by an oil film 56. The droplets of water thus contribute to defining spatially limited, mutually separated amplifying agent areas 54' (FIG. 5c). The droplets of water 54 may be attached to the respective positions on the surface of the carrier 52 by means of hydrophilic coating, so that they will be arranged on the carrier 52 in a defined spatial arrangement. For example, the carrier 52 may comprise a regular pattern of hydrophilic dots which corresponds to the arrangement of the samples of biochemical molecules. The droplets of water 54 have an amplifying agent introduced therein in each case. Thus, for each sample in the form of the particle 50 comprising the DNA bound thereto, a spatially limited amplifying agent area is provided which is separated from the amplifying agent areas of the other samples by the phase boundaries between the liquids, e.g. water and oil. As is shown in FIG. 5b, a carrier 60 comprising binding adapters 62 is provided. The carrier 60 comprising the binding adapters 62 is pressed onto the oil film 56, so that the oil, which is thinner-bodied than water, is displaced, and such that the carrier 60 does not come into contact with the droplets of water 54 with that surface which comprises the binding adapters 62. Said droplets of water 54 may be easily compressed in the process, as is depicted in FIG. 5c.

Subsequently, the DNA that is bound to the particles within the droplets 54 is amplified by means of the amplifying agent so as to create DNA copies. Said DNA copies 64 are bound to the binding adapters 62 and removed from the substrate 52 together with the carrier 60. The carrier 60 having the copied DNA samples 64 bound thereto thus represents a replicate of the original array.

In alternative embodiments, binding adapters may be provided on the substrate 52 rather than on the carrier 60, so that the DNA is copied to the substrate 52, whereas the carrier 60 merely serves as a counter support. This embodiment, too, therefore enables producing a planar microarray as a copy of a particle array while using a water-in-oil emulsion PCR. Thus, fast production of a DNA array is possible. Also, RNA copies, protein copies or modified DNA copies may be produced.

In accordance with the invention, a spatially limited effective area is produced for each sample of the array to be copied, i.e. for which a replicate or derivative is to be created. The spatial creation of the effective area may be performed in various ways. In embodiments of the invention, a spatially closed cavity is provided for each sample. In embodiments, a spatial demarcation may be provided which facilitates diffusion in specific directions, and impedes diffusion in other directions, such as an arrangement of columns or trenches, for example. In embodiments, a porous material, a diffusion-defining material or molecular structures which prefer or restrict diffusion in specific directions may be used, such as hydrogels, aerogels or polymer surfaces. In embodiments, ordered or unordered nano- or molecular structures such as polymer branches, dendrimers, particle arrays, filter membranes, lipid membranes (spherical or planar) may be used so as to implement spatially limited effective areas.

In embodiments, physical fields such as electrical or magnetic fields which also create an advantageous direction of diffusion (electrophoreses, optical tweezers, magnetophoresis, surface acoustic waves, thermophoresis, . . . ) or a diffusion barrier and, thus, build a spatial separation may be used so as to create spatially limited effective areas. For example, a magnetic liquid and "hardening" magnetic fields may be used, or a laser light grid which separates the individual areas.

In embodiments, activation and/or deactivation may take place within or outside the effective areas in order to create spatially limited effective areas, e.g. by means of electrical fields, charge, a change in the pH, deactivation/activation by means of light, pressure and the like. For example, light activation of the polymerase or creation of activated nucleotides by light may be performed within a limited area. No reaction will then take place in the dark areas.

In further embodiments, surface structures may be used which provide a spatially limited effective area with specific physical effects. For example, hydrophobic/hydrophilic areas (e.g. oil and water) or polymers may be mentioned in this context which may swell and harden in specific areas due to electrical fields, and which thus may also define spatially limited effective areas.

Figure 6A:
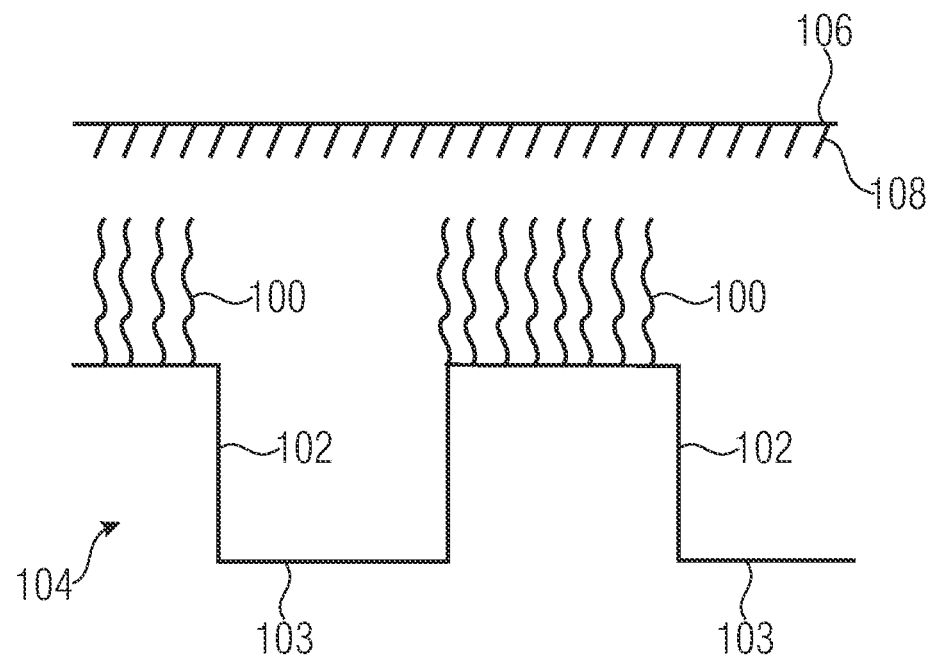
FIGS. 6a to 6d schematically show cross-sectional representations for illustrating a further embodiment of the inventive method.
Figure 6B:
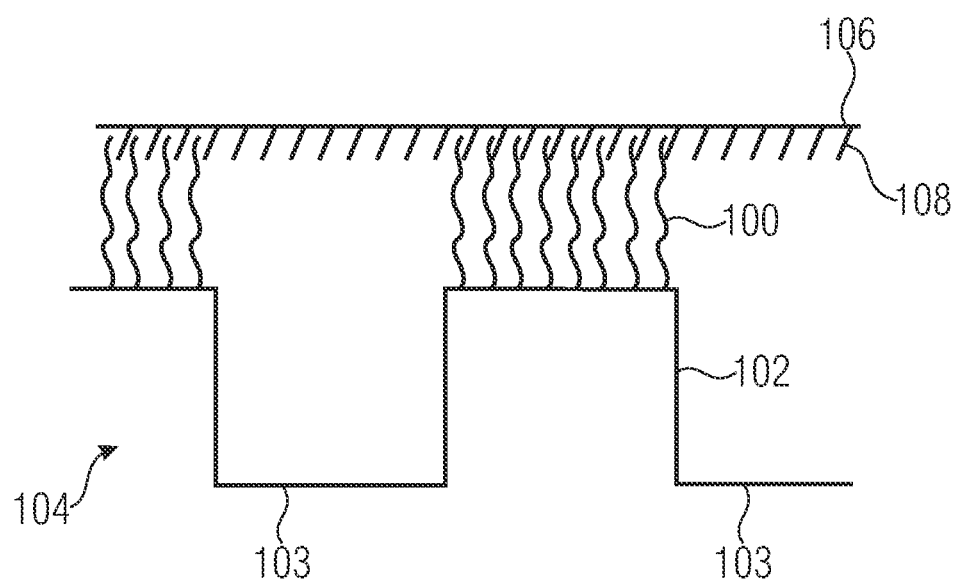

A further embodiment wherein a spatially limited effective area is defined by a three-dimensional structure will now be described with reference to FIGS. 6a to 6d. As is shown in FIG. 6a, samples 100 of molecules that are part of an array are arranged on elevations 102 of an array substrate 104. Between the elevations 102, depressions 103 are formed within the array substrate 104. A carrier 106 comprising binding adapters 108 in the form of a solid-phase primer is placed in the vicinity of the array substrate 104, as is shown in FIG. 6b. Due to the spatial vicinity of the array substrate 104 and of the carrier 106, spatially limited effective areas arise, in the area of the elevations 102, between the opposite surfaces of the elevations 102 and of the carrier 106. By contrast, the spacing between opposite surfaces of the depressions 102 and of the carrier 106 is sufficiently large so that here, no effective area forms.

Figure 6C:
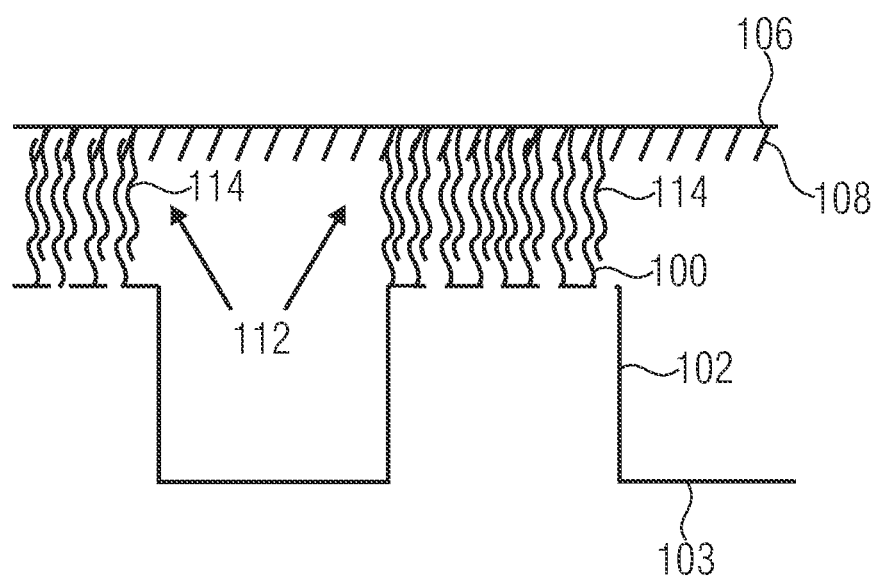
Figure 6D:
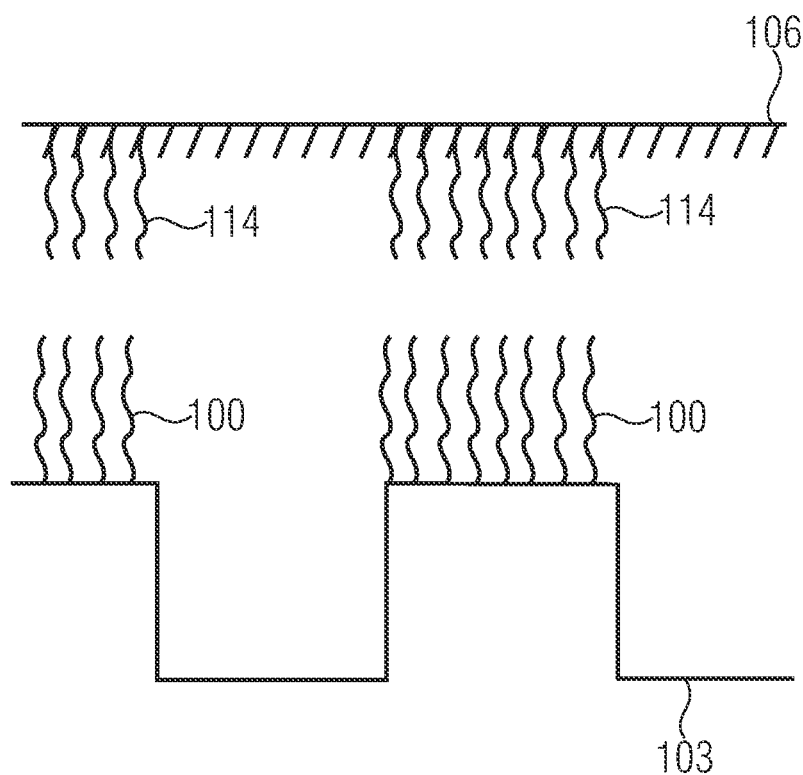

In the effective areas, the contact between the solid-phase primer and the samples 100 enables hybridizing, so that an amplification may start, as is shown in FIG. 6c. Material for the amplification may be additionally supplied from the depressions, as is indicated in FIG. 6c by arrows 112. In this manner, replicates 114 of the samples 100 bound to the carrier 106 are produced, and, thus, a replicate of the array formed by the samples 100 is produced.

Starting from the state depicted in FIG. 6c, the array substrate 104 and the carrier 106 may now be separated, the samples 100 remaining at the array substrate 104, and the replicates 114 being removed with the carrier 106. Further copies may then be made either of the array located on the array substrate 104, or of the replicate located on the carrier 106.

In the embodiment described with reference to FIGS. 6a to 6d, an amplification and a transfer to the carrier take place essentially simultaneously. If transfer and amplification take place separately from each other, one step may be performed, in alternative embodiments, over a large surface area, and the other may be performed in a spatially defined manner.

In the embodiment described with reference to FIGS. 6a to 6d, the spatially limited effective areas are thus produced by the structures described as well as by the presence of a primer. In this context, the reaction corresponds to a bridge amplification. The surfaces are brought into physical contact with one another. Due to the spatial proximity, an "effective area", wherein the DNA is copied to the other surface, forms at the elevations, i.e. the peaks of the columns. Subsequently, said peaks may even be removed, since the amplification is then a classical bridge amplification which defines its own effective area, as it were. However, the start of the reaction comes about only due to the initial condition of the spatial effective area. This reaction might be referred to as an edge or peak amplification. The spatial edge or peak starts off the reaction. The empty space next to the edge supplies the reaction with any materials needed.

In an alternative embodiment, the array to be copied may be arranged, in deviation from FIGS. 6a to 6d, on a planar substrate, whereas the elevations are formed on the carrier to which the array is copied. Again, alternatively, elevations may be formed both on the array substrate and on the carrier.

Figure 7:
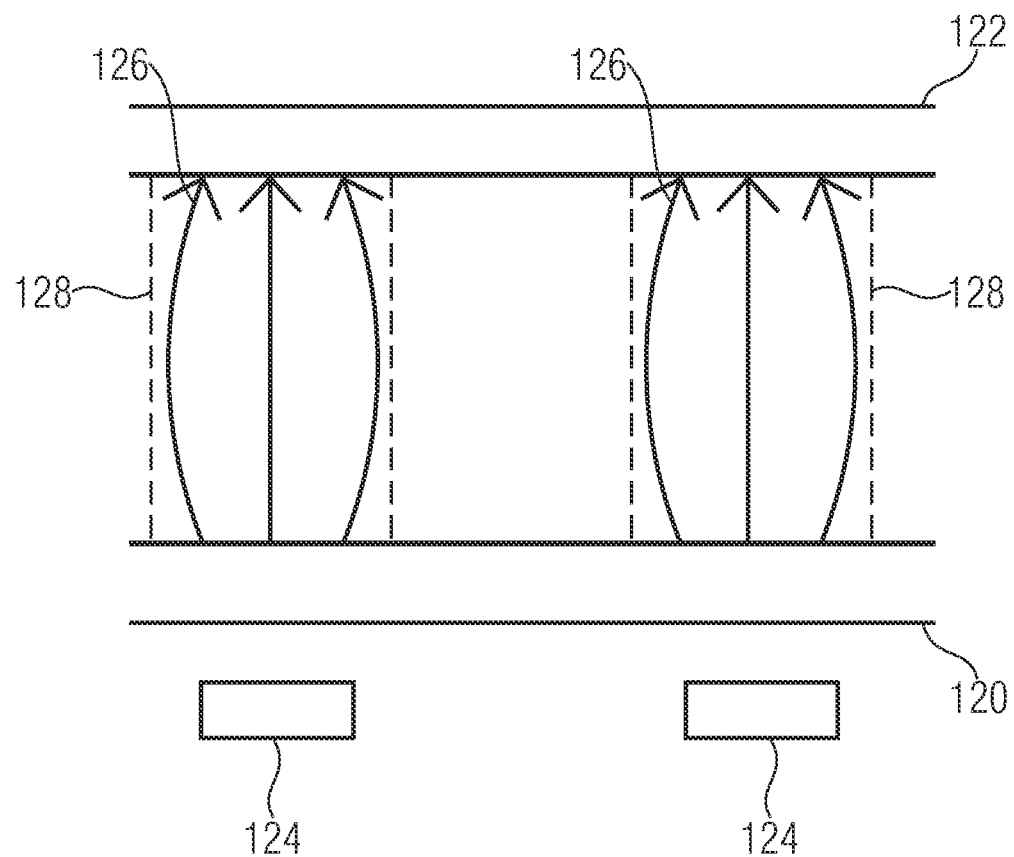
FIG. 7 shows a schematic representation for illustrating a further embodiment of the invention.

An embodiment referring to how spatially limited effective areas may be produced by energy fields, for example magnetic or electrical fields, is depicted in FIG. 7. FIG. 7 merely shows, schematically, an array substrate 120 and a carrier 122. Molecule samples on the array substrate 120 that are to be copied as well as binding adapters on the carrier 122 are not depicted for simplicity's sake. In the area of respective samples of molecules, field generation means 124 are arranged which are configured to generate energy fields 126 in an amplifying agent arranged between the array substrate 120 and the carrier 122. In this manner, spatially limited effective areas 128 are created wherein the amplifying agent is activated, whereas this is not the case in the remaining areas.

Embodiments of inventive methods have been illustrated above. Embodiments of corresponding devices or means for implementing the inventive method steps result from the description or are obvious to a person skilled in the art. Therefore, there is no need to further illustrate that an inventive device may comprise suitable handling means for positioning the physical entities, e.g. the various arrays, carriers or substrates, as needed. In addition, it is not needed to further explain that suitable fluidic means may be provided so as to supply the respective liquids or agents at the needed positions. In addition, it is obvious to a person skilled in the art that a corresponding controller may be provided to control the device to perform the inventive methods. Means for creating an environment needed for performing the methods, for example temperature sensors, may also be provided.

Embodiments of the invention are suited, in particular, to create a replicate or derivative of arrays wherein the molecules are single- or double-stranded oligonucleotides, polynucleotides, DNA or synthetic molecules analogous to DNA (PNA). In embodiments of the invention, a spatially planar arrangement, such as a microarray, a spatial arrangement of particles, for example within a sequencer chip, a spatial arrangement of cavities, for example within a PicoTiterPlate™, or a spatial arrangement of different phases, for example of individual droplets of liquid, may serve as the primary array. In addition, particle-based assays, such as by the companies of Illumina or Applied Biosystems (SOLID), for example, may also be regarded as such types of arrays. In embodiments, the biochemical molecules, for example the oligo- or polynucleotides, may be copied from a sequencing process for deriving the genome, from a sequencing process for deriving the transcriptome, from a process of sequencing RNA (such as mRNA, tRNA, siRNA or RNA in general), or from a process of sequencing mutations and variations. The copies produced may be, in embodiments of the invention, DNA, modified DNA (extended, shortened, artificial, inserts, deletion, mutation . . . ), DNA constructs (expression vectors, siRNA), artificial molecules (PNA, modified peptides), expressions, RNA or proteins, in each case for producing an array.

In embodiments of the invention, oligo- or polynucleotides may be copied from a sequencing process for generating an array or a structured surface. In embodiments, oligo- or polynucleotides may be copied from an arrangement of particles for producing an array or for coating a surface. In embodiments of the invention, oligo- or polynucleotides may be copied from a surface for creating a copy, for creating a complementary copy, or for physicochemically modifying the surface.

In embodiments of the present invention, oligo- or polynucleotides may be copied to a further surface for the purpose of chemical or biochemical modification for an application on the basis of the new surface properties, or for biochemical process chains for producing chemical substances. In embodiments of the invention, a particle array that may, but need not, be produced, for example, by means of a water-in-oil emulsion PCR may be copied, without having to be sequenced, for producing an array of a DNA library, for producing an array comprising various DNA mutants, for further copying said arrays to RNA or proteins, or for using the copies in cellular experiments.

Embodiments of the invention may be employed in numerous fields of application. Examples of such fields of application are sequencing, transcript analysis, measuring DNA, RNA or protein activity, expression studies, display techniques while employing phage displays, ribosome displays or cell displays, and metabolite studies. In addition, the invention may be applied in interaction studies, for example in the following: DNA/DNA; DNA/RNA; DNA/protein; RNA/protein; RNA/cell; protein/protein; kinase activity; protease activity; phosphatase activity; DNA-binding proteins; epitope mapping; determination of pathogens; and determination of substances or inhibitors. The invention may enable this analysis which is partially not possible today with a large number of interaction partners on the array side.

In addition, the present invention may be applied in the field of vaccine development, one example being as follows. Let us assume that a new virus/bacterium appears. A cell sample or a blood sample is taken from the first living being that survives. The cell sample is infected with the virus, and the mRNA is isolated. Said mRNA is then sequenced, and the DNA obtained is copied out from it. Subsequently, the DNA array is transcribed into a protein array. In this manner, this array will contain proteins of the cell and proteins that are modified due to the virus attack. The blood sample is placed onto the array, and the antibodies contained therein bind to the proteins. Only antibodies will bind to the viral proteins, since the antibodies per se do not bind to proteins of the same body. The bound antibodies may then be identified by means of a dying step. Thus, the DNA and protein sequences of the virus can be determined. In this manner, one has gained knowledge, within a very short period, about epitopes and binding proteins of the antibodies. With this information, therefore, both passive and active vaccines can be produced immediately. In this manner, in the event of an epidemic, the time taken before a vaccine can be produced may be reduced dramatically.

Embodiments of the present invention therefore enable a complete work cycle wherein the array of DNA sequences (primary array) that is produced during a sequencing process is to be transferred to a surface, and wherein, thus, a copy of this DNA (secondary array) is to be produced. In addition, in embodiments, the primary or secondary array additionally is to be modeled as a further copy in the form of RNA or protein (tertiary array). In embodiments, each array of biochemical molecules, such as DNA, may be regarded as a primary array. Also, by suitably selecting the copying technique, an identical or selective copy of the original may be produced. Therefore, embodiments of the invention relate to mapping—even prior to, during or after gene sequencing—the array used in the process, and to optionally reforming it into a gene, cDNA, RNA or even protein array in further copying steps.

Embodiments of the invention are advantageous in that molecular information may be replicated, in a spatially resolved manner, any number of times even during a sequencing process. Only one original is needed as a master for this purpose. No information needs to exist about the nature of the original and the data contained therein. The copying process is therefore independent of the information included. In addition, embodiments of the invention allow producing microarrays or copying biochemical surface structurings without employing in-situ syntheses or printing/dispensing units. The copying process takes place at a molecular level and uses well-established biochemical systems. Since the positional information is retained, the copying process allows highly parallel processing of the biochemical information. This enables connecting different types of microarrays at a molecular level and circumvents the time-consuming and costly production of microarrays after gaining knowledge of a sequence.

In embodiments of the invention, micro- or nanostructures which contribute to defining spatially limited amplifying agent areas comprise an unordered matrix based, in particular, on a filter membrane, on a hydrogel or on an aerogel. In embodiments of the invention, the micro- or nanostructures are based on an ordered three-dimensional substrate.

In embodiments of the invention, the spatially limited amplifying agent areas are separated, at least in part, by phase boundaries between two fluids, a fluid and a gas, or a physical boundary, in particular a lipid membrane.

In embodiments of the invention, the process of binding the replicates or derivatives to the carrier may also be performed simultaneously with the amplification, or be part of the amplification, in that an immobilized binding adapter acts as a primer for the amplification. In addition, derivatives may be bound to the carrier via an immobilized capture molecule, or in that they remain coupled to the system used for producing them, and in that said system is immobilized on the carrier. This system may consist of enzymes, ribosomes or cells, for example.

In embodiments of the invention, the spatial limitation of the effective area consists in that the binding adapters are present on the carrier, as complementary primers, in the form of a primer array that may comprise a regular or irregular distribution of spots, the spot size and spot density on the carrier being equal to or smaller than that on the array.

In embodiments of the invention, the amplifying agent is configured to effect a DNA amplification, in particular a polymerase chain reaction, an isothermal amplification, e.g a NASBA reaction, and the binding adapter comprises a matching primer.

In embodiments of the invention, primary, secondary and/or tertiary derivatives are generated, from a primary array or a replicate of the primary array, in that DNA is transcribed into RNA, the RNA is translated into protein, or in that a binder is enriched while using a produced protein, a produced RNA or a produced DNA or the copy thereof from a liquid phase, or in that a binder interacts.

In embodiments of the invention, a derivative is generated on the solid phase of a target array, and is present there in an immobilized manner. In embodiments of the invention, the positions of the samples have further molecules or DNA sequences or cells located thereat which are part of the sample or are immobilized and which are needed for generating derivatives, in particular expression vector sequences such as ori, promoters, ribosome binding sites, start codon, endoprotease cleaving sites, fusion sequences, reporter genes, terminators, antibiotics resistance genes, in-vitro translation systems, or cells.

Embodiments of the invention relate to a replicate or derivative of an array of molecules that was produced while employing an inventive method, and to applications of such a replicate or derivative. In embodiments of the invention, such a replicate or derivative is used for associating a reaction between a binder, in particular a protein, antibody or antigen, and an original molecule, its replicate or its derivative, with the DNA sequence of the original molecule, in particular for genotype-phenotype coupling. In embodiments of the invention, such a replicate or derivative is used for associating a reaction wherein the original molecule, its copy or its derivative catalyzes the conversion of a substrate, with the DNA sequence of the original molecule, in particular for genotype-phenotype coupling. Embodiments of the invention relate to a DNA sequence identified by such an utilization, and to products or preparations produced on the basis of such a DNA sequence, in particular antibodies, antigens, vaccines or antibiotics.

In embodiments of the invention, a replicate or derivative that was produced in accordance with an inventive method is used for detecting reactions between a sample, a replicate or derivative thereof with an interacting molecule or particle, said detection being performed by an optical, electrochemical or magnetic sensor, and the interacting molecule or particle carrying a corresponding marker, or said detection being performed, without any marker, via the change in the evanescent field or a modified resonance frequency, or by employing optical tweezers, or by coupling the reaction with a change in absorption, in particular precipitation or change of color, or with the emission of light, in particular chemiluminescence. In embodiments of the invention, an identical sequencing device that is used for detecting the sequencing is also used for detecting the reactions.

Embodiments of the invention relate to utilization of a corresponding replicate or derivative for performing reactions on the replicate or derivative of the array, a chamber or fluidic structure comprising connecting terminals being applied over the surface of the replicate or derivative, or the replicate or derivative being introduced into a corresponding chamber, it being possible to incubate the chamber at a specific temperature, and to replace liquids contained within the chamber. Such utilization may also take place in a device that is also used for sequencing the array.

Embodiments of the invention relate to utilization of a corresponding replicate or derivative for simultaneously performing reactions and detections on the replicate or derivative. Embodiments of the invention relate to a method of sequencing a liquid-particle array, a replicate being created from samples contained on particles, and the replicate being sequenced in a sequencing device.

In embodiments of the invention, the progress of the reaction may be read out, during the amplification or binding process, by using standard methods. This enables applications in the fields of enzyme, binding and reaction kinetics. For example, an enzyme that binds $CO_2$ may be produced. Said enzyme might then be immediately identified by at a change in the pH value. Similarly, other enzymatic or catalytic activities or binding properties might be identified. These include, as it were, any biochemical measuring techniques measuring the mere presence of a molecule up to its mode of action. Embodiments of the invention therefore comprise monitoring any changes in physical or chemical parameters using well-known detection methods within the individual effective areas during the application, which enables a level of insight into the operating mechanisms of both the amplifying agent and the primary array as well as its derivatives that has hitherto not existed.

Embodiments of the invention provide for the utilization of a replicate or derivative of an array of molecules that was produced while using a method according to the invention for identifying a DNA sequence, a RNA sequence, a protein or a catalytic, signaling (e.g. enhancing, allosteric, inhibiting . . . ) or enzymatic (e.g. lytic, phosphatase activity, kinase activity . . . ) function of a DNA, RNA or protein.

Embodiments of the invention provide for the utilization of a replicate or derivative of an array of molecules that was produced while using a method according to the invention for identifying a DNA sequence, a RNA sequence or peptidic sequence and for producing, identification or preparation of a product, in particular antibody, antigen, vaccine or antibiotic, on the basis of the DNA, RNA or peptidic sequence.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

BIBLIOGRAPHY

[1] Yu A. A. et al, "Contact Printing Beyond Surface Roughness: Liquid Supramolecular Nanostamping", Adv. Mater. 2007, 19, pages 4338 to 4342;
[2] Blanchard A. P., Friend. S. H., Nature Biotech (1999) 17, Page 953 et seq.
[3] Web site: http://www.techno-preneur.net/technology/New-technologies/life-sciences/novel.htm
[4] WO 2008/022332 A2
[5] Kim J., Crooks R., JACS, 128, pages 12076 to 12077 (2006) describe copying of a DNA array using a streptavidin/biotin system
[6] Kim J., Crooks R., Anal Chem (2007) 1, 79: pages 8994-8999;
[7] He M. et. al, Nat Methodes (2008), 5: pages 175-177;
[8] Ramachandran N, et. al; Methodes Mol Biol (2006); 328: pages 1 to 14;
[9] U.S. Pat. No. 6,017,738
[10] U.S. Pat. No. 6,274,351 B1
[11] U.S. Pat. No. 6,300,070 B1;
[12] Abrams E. S. et al, Diagnostic and Gene Detection Ch. 1.9, pages 171-189 (1997);
[13] Laborwelt, edition 3, vol. 8 (2007);
[14] Shendure J. et al., "Next-generation DNA sequencing", Nature Biotechnology, vol. 26, No. 10, October 2008, pages 1135 to 1145;
[15] Handbuch Illumina für den Genome Analyser [*Illumina Handbook for the Genome Analyzer*] (2007);
[16] Kane R. S. et. al, Biomaterials (1999) 20, pages 2363 to 2376;
[17] Torres T. T. et. al., Genome Research, http://genome.cshlp.org/cgi/content/abstract/gr.6984908v1#otherarticles;
[18] EP 1203945 B1

The invention claimed is:

1. A method of producing a replicate or derivative of an array of molecules, the array comprising a spatial arrangement of separate samples of molecules, the method comprising:
creating, for each sample, at least one spatially limited effective area which is separate from the effective areas of the other samples, the effective areas being spatially limited liquid amplifying agent areas, wherein a surface, provided with a binding adapter, of a carrier borders on the effective areas and the binding adapter is immobilized and arranged over an entire area of the carrier;
amplifying the molecules with amplifying agents in the effective areas for creating replicates or derivatives of every one of the samples;
binding the replicates or derivatives of the samples to the carrier with the binding adapter, so that a spatial arrangement of the copies or derivatives of the samples on the carrier corresponds to the spatial arrangement of the samples in the array;

removing the carrier comprising the replicates or derivatives of the samples from the array; wherein the method of creating at least one spatially limited effective area further comprises producing a spatially limited amplifying agent area;

the process of binding the replicates or derivatives to the carrier is performed simultaneously with the amplifying of the molecules; and the method is performed independently of whether any biochemical sequences or information of the array are known or predetermined.

2. The method as claimed in claim 1, wherein the spatially limited amplifying agent areas are defined, at least in part, by micro- or nanostructures within an array substrate of the array or within the carrier, and the micro- or nanostructures comprise an unordered matrix based, on a filter membrane, on a hydrogel or on an aerogel, or wherein the micro- or nanostructures are based on an ordered three-dimensional substrate.

3. The method as claimed in claim 1 wherein, producing at least one spatially limited amplifying agent area for each sample comprises providing the samples in a separated recess within the array substrate, introducing the amplifying agent into the recesses, and closing off the recesses by the carrier, or the spatially limited amplifying agent areas are separated, at least in part, by phase boundaries between two liquids, a liquid and a gas, or a lipid membrane, or the spatially limited amplifying agent areas are separated, at least in part, by phase boundaries between two liquids, a liquid and a gas, or a lipid membrane, and wherein producing at least one spatially limited amplifying agent area for each sample comprises providing the samples in mutually separated droplets of liquid which comprise the amplifying agent and which are fixed, in the spatial arrangement, on an array substrate of the array, a thinner-bodied liquid being arranged between the droplets of liquid, and arranging the carrier in relation to the array substrate such that the surface, provided with the binding adapter, of the carrier borders on the droplets of liquid.

4. The method as claimed in claim 2, wherein producing at least one spatially limited amplifying agent area comprises providing the carrier comprising at least one recess which is associated with each sample and comprises the binding adapter arranged therein, introducing the amplifying agent into the recesses, and closing off the recesses by the array substrate, so that the samples are exposed to the amplifying agent area.

5. The method as claimed in claim 1, wherein producing a spatially limited amplifying agent area for each sample comprises providing the sample within a sequencer chip or a nanowell plate.

6. The method as claimed in claim 1, wherein the spatial limitation of the effective area is that the binding adapter is present on the carrier, as complementary primers, in the form of a primer array that may comprise a regular or irregular distribution of spots, the spot size and spot density on the carrier being equal to or smaller than that on the array.

7. The method as claimed in claim 1, wherein the spatial limitation of the effective area is effected by applying an energy field.

8. The method as claimed in claim 1, wherein the samples are provided in the form of molecules bound to particles.

9. The method as claimed in claim 1, wherein the array of molecules is a non-synthetic array of biomolecules, or the molecules are single- or double-stranded oligonucleotides, polynucleotides, DNA or synthetic molecules analogous to DNA, or the array comprises a sequencing process for deriving the genome, a sequencing process for deriving the transcriptome, a process of sequencing RNA, mRNA, tRNA, siRNA, or a process of sequencing mutations and variations, or by amplifying and binding to the carrier, copies are created which correspond to a DNA, a modified DNA, expressions of a DNA, an RNA, proteins or peptides; or the amplifying agent effects a DNA amplification, a polymerase chain reaction, an isothermal amplification, or a NASBA reaction, and the binding adapter comprises a matching primer, or the method further comprises monitoring any changes in physical or chemical parameters within the effective areas.

10. The method as claimed in claim 1, wherein the spatially limited effective areas comprise further molecules or DNA sequences or cells located therein which are part of the sample or are immobilized and which are needed for generating derivatives including expression vector sequences ori, promoters, ribosome binding sites, start codon, endoprotease cleaving sites, fusion sequences, reporter genes, terminators, antibiotics resistance genes, in-vitro translation systems, or cells.

11. The method as claimed in claim 1, wherein primary, secondary and/or tertiary derivatives are generated, from a primary array or a replicate of the primary array, in that DNA is transcribed into RNA, the RNA is translated into protein, or in that a binder is enriched while using a produced protein, a produced RNA or a produced DNA or the copy thereof from a liquid phase, or in that a binder interacts, or a derivative is generated on the solid phase of a target array and is present there in an immobilized manner.

12. The method as claimed in claim 1, the method further comprising:

(i) associating a reaction between a binder, a protein, antibody or antigen, and an original molecule, its replicate or its derivative, with the DNA sequence of the original molecule, for genotype-phenotype coupling, or (ii) associating a reaction wherein the original molecule, its copy or its derivative catalyzes the conversion of a substrate, with the DNA sequence of the original molecule, for genotype-phenotype coupling, or (ii) identifying a DNA sequence, a RNA sequence, a protein or a catalytic function, a signaling function, or an enzymatic function of a DNA, RNA or protein, or (iv) identifying a DNA sequence, a RNA sequence or a peptidic sequence and for producing, identification or preparation of a product, antibody, antigen, vaccine or antibiotic, on the basis of the DNA, RNA or peptidic sequence, or (v) detecting reactions between a sample, a replicate or derivative thereof with an interacting molecule or particle, said detection being performed by an optical, electrochemical or magnetic sensor, and the interacting molecule or particle carrying a corresponding marker, or said detection being performed, without any marker, via the change in the evanescent field or a modified resonance frequency, or by employing optical tweezers, or by coupling the reaction with a change in absorption, precipitation or change of color, or with the emission of light, chemiluminescence, or
(vi) performing reactions on the replicate or derivative of the array, a chamber or fluidic structure comprising connecting terminals being applied over the surface of the replicate or derivative, or the replicate or derivative being introduced into a corresponding chamber, it being possible to incubate the chamber at a specific temperature, and to replace liquids comprised within the chamber, or
(vii) simultaneously performing reactions and detections on the replicate or derivative.

13. The method as claimed in claim 12, wherein a sequencing device that is used for sequencing the array of molecules is also used for each of steps (i)-(vii).

* * * * *

UNITED STATES PATENT AND TRADEMARK OFFICE
CERTIFICATE OF CORRECTION

PATENT NO.        : 9,725,758 B2
APPLICATION NO. : 13/224645
DATED             : August 8, 2017
INVENTOR(S)      : Zengerle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 261 days.

Signed and Sealed this
Twenty-fifth Day of September, 2018

Andrei Iancu
*Director of the United States Patent and Trademark Office*